(12) United States Patent
Wang et al.

(10) Patent No.: US 11,299,709 B2
(45) Date of Patent: Apr. 12, 2022

(54) PLURIPOTENT STEM CELL AND T CELL DIFFERENTIATED THEREFROM AND APPLICATION THEREOF

(71) Applicant: GUANGZHOU INSTITUTES OF BIOMEDICINE AND HEALTH CHINESE ACADEMY OF SCIENCES, Guangdong (CN)

(72) Inventors: Jinyong Wang, Guangdong (CN); Rongqun Guo, Guangdong (CN); Mengyun Zhang, Guangdong (CN); Lijuan Liu, Guangdong (CN); Xiaofei Liu, Guangdong (CN); Cui Lv, Guangdong (CN); Juan Du, Guangdong (CN)

(73) Assignee: GUANGZHOU INSTITUTES OF BIOMEDICINE AND HEALTH CHINESE ACADEMY OF SCIENCES, Guangdong (CN)

( * ) Notice: Subject to any disclaimer, the term of this patent is extended or adjusted under 35 U.S.C. 154(b) by 574 days.

(21) Appl. No.: 16/312,794

(22) PCT Filed: Jan. 11, 2018

(86) PCT No.: PCT/CN2018/072254
§ 371 (c)(1),
(2) Date: Dec. 21, 2018

(87) PCT Pub. No.: WO2019/127664
PCT Pub. Date: Jul. 4, 2019

(65) Prior Publication Data
US 2020/0208107 A1   Jul. 2, 2020
US 2021/0238548 A9   Aug. 5, 2021

(30) Foreign Application Priority Data

Dec. 30, 2017 (CN) .......................... 201711490483.8

(51) Int. Cl.
A61K 39/00 (2006.01)
A61K 35/17 (2015.01)
C12N 5/0783 (2010.01)
C12N 15/85 (2006.01)
C12N 15/90 (2006.01)

(52) U.S. Cl.
CPC ............ *C12N 5/0636* (2013.01); *A61K 35/17* (2013.01); *C12N 15/85* (2013.01); *C12N 15/907* (2013.01); *C12N 2500/00* (2013.01); *C12N 2500/24* (2013.01); *C12N 2501/115* (2013.01); *C12N 2501/125* (2013.01); *C12N 2501/145* (2013.01); *C12N 2501/155* (2013.01); *C12N 2501/16* (2013.01); *C12N 2501/165* (2013.01); *C12N 2501/2303* (2013.01); *C12N 2501/2306* (2013.01); *C12N 2501/26* (2013.01); *C12N 2501/999* (2013.01); *C12N 2502/1394* (2013.01); *C12N 2506/02* (2013.01); *C12N 2506/45* (2013.01); *C12N 2510/00* (2013.01)

(58) Field of Classification Search
None
See application file for complete search history.

(56) References Cited

U.S. PATENT DOCUMENTS 10,865,381 B2 * 12/2020 Yu .................... C12N 5/0637
2017/0107492 A1 *  4/2017 Yu .................... C12N 5/0636
2019/0119643 A1 *  4/2019 Daley ................... A61K 35/44

FOREIGN PATENT DOCUMENTS

| JP | 2016513974 | 5/2016 |
| WO | WO2017070333 | 4/2017 |
| WO | WO2017192708 A1 | 11/2017 |

OTHER PUBLICATIONS

Google Search D0 medium, D2.5 medium D3 medium D4 medium D5 medium pp. 1-2; downloaded Sep. 22, 2021.*
T-cell receptor—Wikipedia p. 1 of 16; downloaded Sep. 22, 2021.*
Holmes et al., 2009 The OP9-DL1 system: generation of T-lymphocytes from embryonic or hematopoietic stem cells in vitro.*
De Smedt et al., Human bone marrow CD34+ progenitor cells mature to T cells on OP9-DL1 stromal cell line without thymus microenvironment; Blood Cells, Molecules, and Diseases 33 (2004) 227-232.*
Sugimura, R. Haematopoietic stem and progenitor cells from human pluripotent stem cells. Nature. May 25, 2017 (May 25, 2017), 432-438.
Tsuzuki, S. Expansion of functionally defined mouse hematopoietic stem and progenitor cells by a short isoform of RUNX1/AML1. Blood. Jan. 19, 2012 (Jan. 19, 2012) 727-735.
Kuvardina, O.N. Hematopoietic transcription factors and differential cofactor binding regulate PRKACB isoform expression. Oncotarget. Apr. 24, 2017 (Apr. 24, 2017) 71685-71698.
Chen, B. Inducible overexpression of RUNX1 b/c in human emryonic stem cells blocks early hematopoiesis from mesoderm. Journal of Molecular Cell Biology. Aug. 9, 2017 (Aug. 9, 2017) 262-273.
Sandler, V.M. Reprogramming human endothelial cells to haematopoietic cells requires vascular induction. Nature. Jul. 17, 2014 (Jul. 17, 2014) 312-318.
Lis, R. Conversion of adult endothelim to immunocompetent haematopoietic stem cells. Nature, May 25, 2017 (May 25, 2017) 439-445.

(Continued)

*Primary Examiner* — Maria G Leavitt
(74) *Attorney, Agent, or Firm* — Workman Nydegger

(57) ABSTRACT

The present invention provides a pluripotent stem cell comprising a co-expression vector in which Runx1 and Hoxa9 are of in tandem, and a T cell differentiated therefrom and application thereof. In the present invention, Pluripotent stem cells inducibly co-expressing exogenous Runx1 and Hoxa9 are successfully established by introducing an exogenous vector co-expressing Runx1 and Hoxa9 into pluripotent stem cells. The pluripotent stem cells are directionally differentiated into T-lineage progenitor cells and will be developed into T cells. The pluripotent stem cell-derived T cells obtained by the method of the present invention are not only functionally normal but also have no tumorigenic risk.

10 Claims, 13 Drawing Sheets

(56) References Cited

OTHER PUBLICATIONS

"Construction and expression of key transcription factors involved in hematopoiesis in lentivirus" Zhen, Wang Shandong Normal University, Dissertation Part I & Part II, 2013.

Guo, Rongqun, et al., "Guiding T lymphopoiesis from pluripotent stem cells by defined transcription factors", *Cell Research*, Nov. 15, 2019.

Panepucci, Rodrigo Alexandre, et al., "Increased Levels of NOTCH1, NF-kB, and Other Interconnected Transcription Factors Characterize Primitive Sets of Hematopoietic Stem Cells", Stem Cells and Development, vol. 19, Nov. 3, 2010.

Japanese Office Action cited in Application No. 2020-535615 dated Jul. 9, 2021.

International Search Report issued in PCT/CN2018/072254 dated Aug. 15, 2018.

Navarro- Montero, O. RUNX1c Regulates Hematopoietic Differentiation of Human Pluripotent stem Cells Possibly in Cooperation with Proinflammatory Signaling. Stem Cells. Sep. 4, 2017, 2253-2266.

\* cited by examiner

Sorting strategy for hematopoietic stem cell precursors

Hematopoietic stem cell precursors were sorted for co-culture

The morphology of cobblestone-like areas after 10 days of co-culture of the sorted hematopoietic precursor cells

PLURIPOTENT STEM CELL AND T CELL DIFFERENTIATED THEREFROM AND APPLICATION THEREOF

TECHNICAL FIELD

The invention belongs to the technical field of medical bio-engineering and relates to a pluripotent stem cell and a T cell differentiated therefrom and application thereof.

BACKGROUND

Pluripotent stem cells (PSCs), which are currently the focus in stem cell research, are a class of cells with unlimited proliferative potential, having the ability to differentiate into different lineages of cellular tissues, and are easily genetically modified. Inducing autologous pluripotent stem cells to differentiate into different tissues is an application hotspot in the field of regenerative medicine, which can not only avoid ethical controversy, but also reduce the risk of immune rejection. As an emerging immune cell therapy, CAR-T has received extensive attentions due to the characteristics of high specificity and high cancer cell removal efficiency. At present, the immune cells for the CAR-T therapy are mainly derived from the patient's own T cells. However, some patients (such as infants, immunodeficiency patients with advanced tumor and patients received extensive chemotherapy) are unable to provide effective doses of T cells and the CAR-T therapy is expensive, greatly limiting the application of this therapy. The above problems can be solved by obtaining functional T cells by pluripotent stem cells.

A basic research has been carried out to obtain hematopoietic stem and progenitor cells (HSPCs) with multilineage hematopoietic reconstitution ability by expressing transcription factors ERG, HOXA5, HOXA9, HOXA10, LCOR, RUNX1 and SPI1 in the human pluripotent stem cell-derived hematopoietic endothelium, followed by transplantation to produce multiple hematopoietic lineage cells (including T cells) (R. Sugimura et al. Haematopoietic stem and progenitor cells from human pluripotent stem cells. Nature, 545, 432-438 (2017)). However, the above study requires up to seven transcription factors for stem cell induction, having the disadvantages of complex operation, poor stability and low efficiency.

It has also been reported that human hematopoietic multipotent progenitors having the ability to reconstitute partial lineage haematopoiesis (without the ability to reconstitute T cell lineage haematopoiesis) and mouse hematopoietic stem cells having the ability to reconstitute all lineage haematopoiesis were obtained by expressing transcription factors FOSB, GFI1, RUNX1 and SPI1 in endothelial cells (V. M. Sandler et al. Reprogramming human endothelial cells to haematopoietic cells requires vascular induction. Nature 511, 213-318 (2014); R. Lis et al. Conversion of adult endothelium to immunocompetent haematopoietic stem cells. Nature 545, 439-445 (2017)). However, the above studies have problems such as inconvenient access to endothelial cells, difficulty in gene editing, cumbersome technical methods and low efficiency of T-lineage generation. Therefore, there is a need for a simple method for inducing pluripotent stem cells to solely obtain T lineage cell.

SUMMARY OF THE INVENTION

In view of the deficiencies of the prior art, the present invention provides a pluripotent stem cell and a T cell differentiated therefrom and application thereof. The obtained pluripotent stem cell-derived T cells not only function normally, but also has no tumorigenic risk.

In a first aspect, the present invention provides a vector comprising Runx1 and Hoxa9 in which Runx1 and Hoxa9 are co-expressed in tandem.

In the present invention, the cDNA sequences of Runx1 and Hoxa9 are expressed in tandem in the same vector for infecting host cells, resulting in host cells stably expressing Runx1 and Hoxa9, which are easy to operate and efficient, and the obtained host cells have the ability to differentiate into T cells.

In a second aspect, the present invention provides a nucleic acid expressing the vector as described in the first aspect.

In a third aspect, the present invention provides a host cell comprising the vector as described in the first aspect;

Preferably, the host cell is a pluripotent stem cell.

In a fourth aspect, the present invention provides a method for directed differentiation of T cells using pluripotent stem cells, comprising the steps of:

(1) integrating an expression vector in which Runx1 and Hoxa9 are of in tandem into pluripotent stem cells and performing resistance screening;

(2) directionally differentiating the pluripotent stem cells of step (1) into hematopoietic stem cell precursors;

(3) co-culturing the hematopoietic stem cell precursors of step (2) with mouse bone marrow stromal cells to obtain T-lineage progenitor cells; and (4) inducing the T-lineage progenitor cells of step (3) to differentiate into T cells.

In the present invention, functionally normal T cells with no tumorigenic risk are obtained by subjecting the pluripotent stem cell line co-expressing Runx1 and Hoxa9 to directional differentiation condition to obtain hematopoietic stem cell precursors, which are then co-cultured with the OP9-DL1 cell line to generate T-lineage progenitor cells, followed by further differentiation.

Preferably, the expression vector in which Runx1 and Hoxa9 are in a tandem arrangement in step (1) is integrated into Rosa26 site of the pluripotent stem cells.

Preferably, the pluripotent stem cells in step (1) are genetically-edited inducible pluripotent stem cells and/or embryonic pluripotent stem cell lines.

Preferably, the method for integrating in step (1) comprises any one of homologous recombination, CRISPR/Cas9, TALEN, transfection or viral infection, or combination thereof, preferably homologous recombination.

Preferably, the resistance screening in step (1) employs Hygromycin B.

Preferably, the method for directed differentiation in step (2) is to culture the pluripotent stem cells with D0 medium, D2.5 medium, D3 medium, D4 medium, D5 medium, D6 medium and D7 medium sequentially to obtain the hematopoietic stem cell precursors.

Preferably, the D0 medium is a basic differentiation medium containing 3-8 ng/mL bone morphogenetic protein 4 (BMP4), wherein the concentration of the bone morphogenetic protein 4 may be, for example, 3 ng/mL, 5 ng/mL or 8 ng/mL, preferably 5 ng/mL.

Preferably, the D2.5 medium is a basic differentiation medium containing 3-8 ng/mL activin A and 3-8 ng/mL basic fibroblast growth factor (bFGF), wherein the concentration of activin A may be, for example, 3 ng/mL, 5 ng/mL or 8 ng/mL, preferably 5 ng/mL, and the concentration of the basic fibroblast growth factor may be, for example, 3 ng/mL, 5 Ng/mL or 8 ng/mL, preferably 5 ng/mL.

Preferably, the D3 medium is a basic differentiation medium containing 3-8 ng/mL Activin A, 3-8 ng/mL bone morphogenetic protein 4 (BMP4) and 3-8 ng/mL vascular endothelial growth factor, wherein the concentration of activin A may be, for example, 3 ng/mL, 5 ng/mL or 8 ng/mL, preferably 5 ng/mL, the concentration of the bone morphogenetic protein 4 may be, for example, 3 ng/mL, 5 ng/mL or 8 ng/mL, preferably 5 ng/mL, and the concentration of the vascular endothelial growth factor may be, for example, 3 ng/mL, 5 ng/mL or 8 ng/mL, preferably 5 ng/mL.

Preferably, the D4 medium is a basic differentiation medium containing 3-8 ng/mL bone morphogenetic protein 4 (BMP4) and 3-8 ng/mL vascular endothelial growth factor (VEGF), wherein the concentration of the bone morphogenetic protein 4 may be, for example, 3 ng/mL, 5 ng/mL or 8 ng/mL, preferably 5 ng/mL, and the concentration of the vascular endothelial growth factor may be, for example, 3 ng/mL, 5 ng/mL or 8 ng/mL, preferably 5 ng/mL.

Preferably, the D5 medium is a basic differentiation medium containing 3-8 ng/mL bone morphogenetic protein 4 (BMP4), 3-8 ng/mL vascular endothelial growth factor (VEGF), 10-30 ng/mL recombinant mouse interleukin 3 (mIL3), 10-30 ng/mL recombinant mouse interleukin 6 (mIL6), 10-30 ng/mL recombinant mouse stem cell factor (mSCF), 10-30 ng/mL recombinant human thrombopoietin (hTPO) and 10-30 ng/mL human Fms-associated tyrosine kinase 3 ligand (hFlt3L), wherein the concentration of the bone morphogenetic protein 4 may be, for example, 3 ng/mL, 5 ng/mL or 8 ng/mL, preferably 5 ng/mL, the concentration of the vascular endothelial growth factor may be, for example, 3 ng/mL, 5 ng/mL or 8 ng/mL, preferably 5 ng/mL, the concentration of the recombinant mouse interleukin 3 may be, for example, 10 ng/mL, 20 ng/mL or 30 ng/mL, preferably 20 ng/mL, the concentration of the recombinant mouse interleukin 6 may be, for example, 10 ng/mL, 20 ng/mL or 30 ng/mL, preferably 20 ng/mL, the concentration of the recombinant mouse stem cell factor may be, for example, 10 ng/mL, 20 ng/mL or 30 ng/mL, preferably 20 ng/mL, the concentration of the recombinant human thrombopoietin may be, for example, 10 ng/m L, 20 ng/mL or 30 ng/mL, preferably 20 ng/mL, and the concentration of the hFlt3L may be, for example, 10 ng/mL, 20 ng/mL or 30 ng/mL, preferably 20 ng/mL.

Preferably, the D6 medium is a basic differentiation medium containing 3-8 ng/mL bone morphogenetic protein 4 (BMP4), 3-8 ng/mL vascular endothelial growth factor (VEGF), 10-30 ng/mL recombinant mouse interleukin 3 (mIL3), 10-30 ng/mL recombinant mouse interleukin 6 (mIL6), 10-30 ng/mL recombinant mouse stem cell factor (mSCF), 10-30 ng/mL recombinant human thrombopoietin (hTPO), and 10-30 ng/mL hFlt3L and 1-2 µg/mL Doxycycline (Dox), wherein the concentration of the bone morphogenetic protein 4 may be, for example, 3 ng/mL, 5 ng/mL or 8 ng/mL, preferably 5 ng/mL, the concentration of the vascular endothelial growth factor may be, for example, 3 ng/mL, 5 ng/mL or 8 ng/mL, preferably 5 ng/mL, the concentration of the recombinant mouse interleukin 3 may be, for example, 10 ng/mL, 20 ng/mL or 30 ng/mL, preferably 20 ng/mL, the concentration of the recombinant mouse interleukin 6 may be, for example, 10 ng/mL, 20 ng/mL or 30 ng/mL, preferably 20 ng/mL, the concentration of the recombinant mouse stem cell factor may be, for example, 10 ng/mL, 20 ng/mL or 30 ng/mL, preferably 20 ng/mL, the concentration of the recombinant human thrombopoietin may be, for example, 10 ng/m L, 20 ng/mL or 30 ng/mL, preferably 20 ng/mL, the concentration of the hFlt3L may be, for example, 10 ng/mL, 20 ng/mL or 30 ng/mL, prefer-ably 20 ng/mL, and the concentration of the Doxycycline may be, for example, 1 µg/mL or 2 µg/mL, preferably 1 µg/mL.

Preferably, the D7 medium is a basic differentiation medium containing 10-30 ng/mL recombinant mouse interleukin 3 (mIL3), 10-30 ng/mL recombinant mouse interleukin 6 (mIL6), 10-30 ng/mL recombinant mouse stem cell factor (mSCF), 10-30 ng/mL recombinant human thrombopoietin (hTPO), and 10-30 ng/mL hFlt3L and 1-2 µg/mL Doxycycline (Dox), wherein the concentration of the recombinant mouse interleukin 3 may be, for example, 10 ng/mL, 20 ng/mL or 30 ng/mL, preferably 20 ng/mL, the concentration of the recombinant mouse interleukin 6 may be, for example, 10 ng/mL, 20 ng/mL or 30 ng/mL, preferably 20 ng/mL, the concentration of the recombinant mouse stem cell factor may be, for example, 10 ng/mL, 20 ng/mL or 30 ng/mL, preferably 20 ng/mL, the concentration of the recombinant human thrombopoietin may be, for example, 10 ng/m L, 20 ng/mL or 30 ng/mL, preferably 20 ng/mL, the concentration of the hFlt3L may be, for example, 10 ng/mL, 20 ng/mL or 30 ng/mL, preferably 20 ng/mL, and the concentration of the Doxycycline may be, for example, 1 µg/mL or 2 µg/mL, preferably 1 µg/mL.

Preferably, the basic differentiation medium is IMDM medium comprising 10-20% fetal calf serum, 180-220 µg/mL iron-saturated transferrin, $4.5 \times 10^{-4}$ M thioglycerol, 1-3 mM GlutaMAX™-I (L-alanyl-L-glutamine dipeptide) additive and 0.4-0.6 mM ascorbic acid, wherein the concentration of the fetal bovine serum may be, for example, 10%, 15% or 20%, preferably 15%, the concentration of the iron-saturated transferrin may be, for example, 180 µg/mL, 200 µg/mL or 220 µg/mL, preferably 200 µg/mL, the concentration of the thioglycerol may be, for example, $4 \times 10^{-4}$ M, $4.5 \times 10^{-4}$ M or $5 \times 10^{-4}$ M, preferably $4.5 \times 10^{-4}$ M, the concentration of the GlutaMAX™-I additive may be, for example, 1 mM, 2 mM or 3 mM, preferably 2 mM, and the concentration of the ascorbic acid may be, for example, 0.4 mM, 0.5 mM or 0.6 mM, preferably 0.5 mM.

In the present invention, the inventors designed and optimized the directed hematopoietic differentiation system by changing the additive substances in the medium and induced the hematopoietic differentiation of the pluripotent stem cells into hematopoietic stem cell precursors, which were further co-cultured with mouse bone marrow stromal cells to obtain T-lineage progenitor cells.

Preferably, the stromal cells in step (3) are OP9-DL1 cells.

Preferably, Doxycycline is used for inducing during the co-culture in step (3).

Preferably, the T cells in step (4) are mainly $CD3^+$ T cells.

Preferably, the T cells are TCR β cells and/or TCR γ/δ cells.

As a preferred technical solution, the present invention provides a method for the directional differentiation of pluripotent stem cells into T cells, comprising the steps of:

(1) integrating an expression vector wherein Runx1 and Hoxa9 are linked in tandem into pluripotent stem cells at the Rosa26 site by gene recombination and performing resistance screening with Hygromycin B;

(2) culturing the pluripotent stem cells of step (1) with D0 medium, D2.5 medium, D3 medium, D4 medium, D5 medium, D6 medium and D7 medium sequentially, and directionally differentiating the same into hematopoietic stem cell precursors on day 11;

(3) co-culturing the hematopoietic stem cell precursors of step (2) with OP9-DL1 cells and inducing with Doxycycline to obtain T-lineage progenitor cells; and (4) inducing the T-lineage progenitor cells of step (3) to differentiate into T cells which are TCR β cells and/or TCR γ/δ cells.

In a fifth aspect, the present invention provides a T-lineage progenitor cell and/or a T cell prepared by the method of the first aspect.

In a sixth aspect, the present invention provides a pharmaceutical composition comprising any one of the vector as described in the first aspect, the host cell as described in the third aspect, and the T-lineage progenitor cell or the T cell as described in the fifth aspect or combination thereof.

Preferably, the pharmaceutical composition further comprises any one of a pharmaceutically acceptable carrier, excipient or diluent, or combination thereof.

In a seventh aspect, the present invention provides the pharmaceutical composition according to the fourth aspect for use in the preparation of a medicament for enhancing an immune response, preferably for the preparation of a medicament for enhancing an immune response of a T cell.

In the present invention, the pharmaceutical composition can be used to enhance an immune response, in particular, to enhance the immune response of a T cell.

In an eighth aspect, the present invention provides the pharmaceutical composition according to the fourth aspect for use in preparation of a medicament for preventing and/or treating immunodeficiency, preferably for preparation of a medicament for preventing and/or treating T cell immunodeficiency.

In the present invention, the pharmaceutical composition can be used for preventing and/or treating immunodeficiency, in particular, for preventing and/or treating T cell immunodeficiency.

In a ninth aspect, the present invention provides the pharmaceutical composition according to the fourth aspect for use in preparation of a medicament used for treating a tumor with T cell immunotherapy.

In the present invention, the pharmaceutical composition can be used in a T cell immunotherapy.

Compared with the prior art, the present invention has the following beneficial effects:

(1) Pluripotent stem cells which inducibly co-express exogenous Runx1 and Hoxa9 are successfully constructed in the present invention by introducing an exogenous vector co-expressing Runx1 and Hoxa9 into pluripotent stem cells. The pluripotent stem cells have the ability to differentiate into T cells, and can be used for preparing a medicine for enhancing immune effects, preventing and/or treating immunodeficiency and treating tumors;

(2) A directed differentiation system and a co-culture method are adopted in the present invention to directionally differentiate the pluripotent stem cells into T-lineage progenitor cells which can be induced to differentiate into T cells, and can be used for preparing a medicine for enhancing immune effects, preventing and/or treating immunodeficiency and treating tumors;

(3) The pluripotent stem cell-derived T cells obtained by the method of the present invention function normally without tumorigenic risk, and can be used for preparing a medicine for enhancing immune effects, preventing and/or treating immunodeficiency and treating tumors.

DESCRIPTION OF THE DRAWINGS

FIG. 1 (B) is a light field diagram of the iRunx1-p2a-Hoxa9 pluripotent stem cells which were obtained by resistance screening with Hygromycin; and FIG. 1 (C) shows the relative expression levels of Runx1 and Hoxa9 after 24 hours of treatment with Doxycycline;

FIG. 2 (B) is a diagram showing the cell morphology on day 11 during the induction of the directional differentiation of iRunx1-p2a-Hoxa9 pluripotent stem cells; and FIG. 2 (C) shows the composition and proportion of hematopoietic-related cells on day 11 of the directed differentiation which were analyzed by flow cytometry;

FIG. 3 (B) is a schematic diagram showing co-culture of the sorted hematopoietic stem cell precursor population ($CD31^+CD41^{low}/CD45^-c\text{-}Kit^+CD201^{high}$) and OP9-DL1 cell line; FIG. 3 (C) shows the number of cobblestone-like formation areas observed under the microscope after 10 days of the co-culture of hematopoietic stem cell precursor population with OP9-DL1 cell line; and FIG. 3 (D) shows the light field diagram of the cobblestone-like-like formation areas observed under the microscope after 10 days of the co-culture of hematopoietic stem cell precursor population with OP9-DL1 cell line.

FIG. 4 (B) shows the identification of pluripotent stem cell-derived blood cells by flow cytometry 4 weeks after the transplantation, wherein hematopoietic chimera were detected in the iRunx1-p2a-Hoxa9 group; FIG. 4 (C) shows the lineage distribution of pluripotent stem cell-derived hematopoietic cells and the phenotype of $CD3^+$ T lymphocytes in peripheral blood, bone marrow, spleen and thymus of the recipient mouse which was sacrificed 5 weeks after the transplantation; and FIG. 4 (D) shows the PCR and sequencing identification of the genome of the pluripotent stem cell-derived blood cells.

FIG. 5 (B) shows the analysis for the TCR-β and TCR-γ/δ populations in the pluripotent stem cell-derived $CD3^+$ T cells in the peripheral blood, spleen and lymph nodes of the recipient mouse which was sacrificed 4 weeks after the transplantation; and FIG. 5 (C) shows a mixed lymphocyte reaction (MLR) experiment of the recipient mouse which was sacrificed 4 weeks after the transplantation, wherein the PSC-T is $CD3^+$ T cells enriched in the spleen by magnetic beads 6 weeks after the transplantation of T-lineage progenitor cells which were obtained by inducing the differentiation of pluripotent stem cell line with Runx1-p2a-Hoxa9 into a NOD-SCID recipient mouse.

DETAILED DESCRIPTION

In order to further illustrate the technical measures adopted by the present invention and the effects thereof, the present invention is further described below with reference to the embodiments and accompanying drawings. It can be understand that the specific embodiments described herein are merely illustrative of the invention and are not intended to limit the present invention.

In the examples, techniques or conditions, which are not specifically indicated, are performed according to techniques or conditions described in the literature of the art, or according to product instructions. The reagents or instruments for use, which are not indicated with manufacturers, are conventional products that are commercially available from formal sources.

Example 1

Figure 1A:
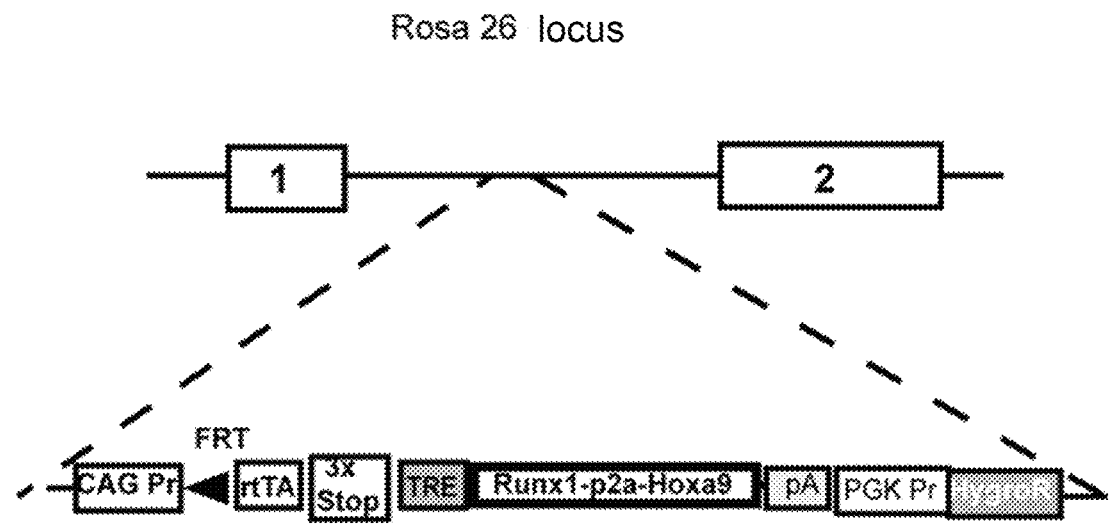
FIG. 1 (A) is a schematic diagram showing an inducible expression system to site-specifically knock-in at the Rosa26 site of pluripotent stem cells. The expression system employed a p2a sequence to link the cDNA sequences of Runx1 and Hoxa9 in tandem, and Doxycycline was used to induce gene expression.
Figure 1B:
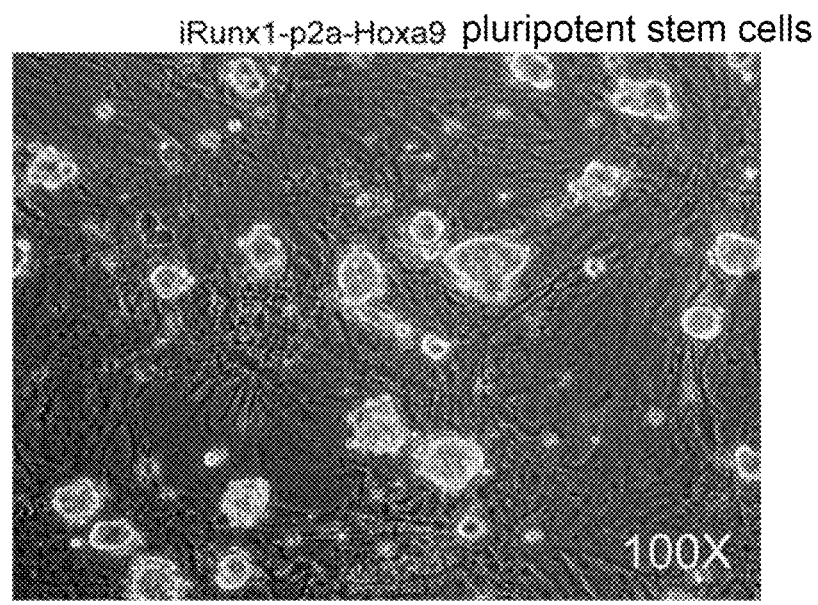
Figure 1C:
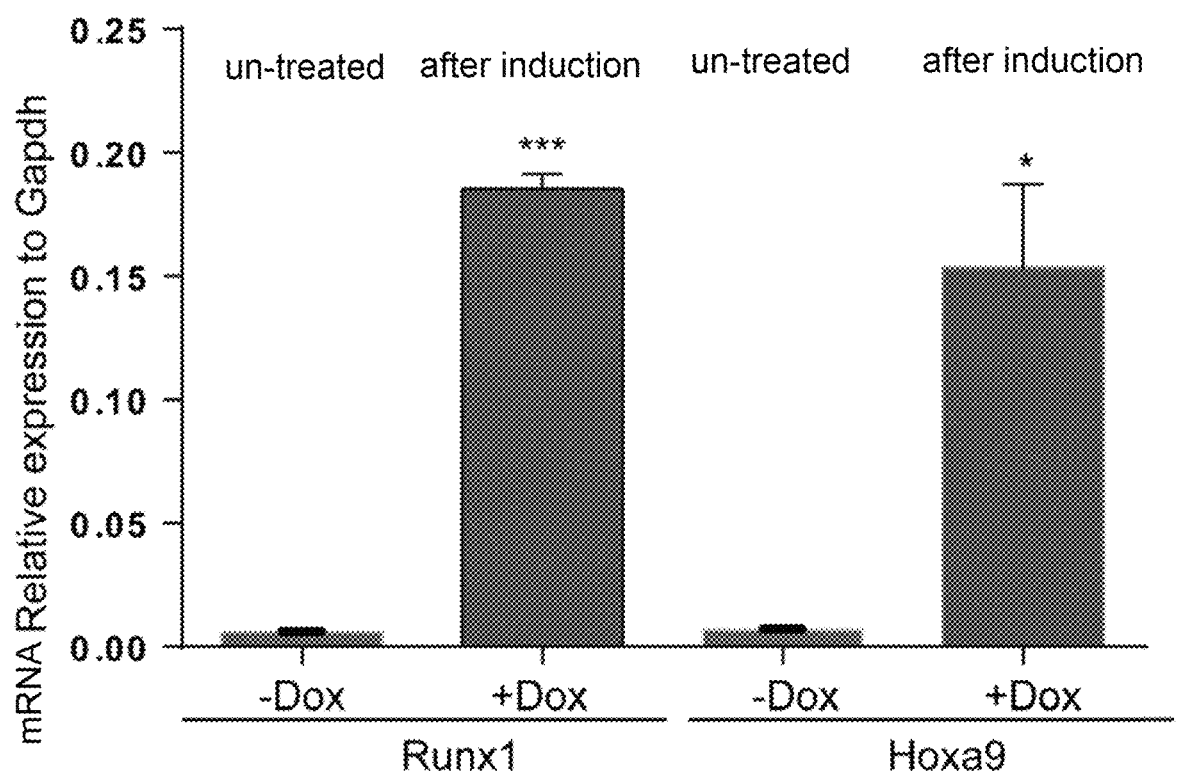

In this example, an inducible expression sequence was site-specifically knocked-in at the Rosa26 site of pluripotent stem cells by electro-transformation in combination with gene recombination, as shown in FIG. 1 (A), wherein the knocked-in sequence comprised Runx1-p2a-Hoxa9 tandem sequence and a Hygromycin B resistance gene sequence for resistance screening. In order to obtain homologous recombined pluripotent stem cells successfully, a pluripotent stem cell medium containing Hygromycin B (150 µg/mL) was added 20 hours after the electro-transformation and the medium was replaced every day. After screening with Hygromycin B for 10 days, individual clones were selected under a microscope into a 12-well plate which was pre-incubated with MEF cells, with one pluripotent stem cell clone per well, and cultured in a Hygromycin-free medium.

The medium was replaced every day when the clone mass was adhered in the MEF cell layer. After 3 days, the clone mass was digested with 0.25% trypsin and passaged into a 12-well plate. The cell morphology was shown in FIG. 1 (B), and the clone mass was in logarithmic growth phase, the edge was neat and transparent, there was a clear boundary with the MEF cell layer and there was no differentiation. The cells were passaged, amplified and frozen according to their state and growth density.

The total mRNA of the iRunx1-p2a-Hoxa9 pluripotent stem cells was extracted after 24 hours of Dox treatment (a Dox-free group was used as a control group), and the expression levels of Runx1 and Hoxa9 mRNA were obtained by Q-PCR. It was shown in FIG. 1 (C) that the addition of Dox could induce the expression of Runx1 and Hoxa9.

Example 2

Figure 2A:
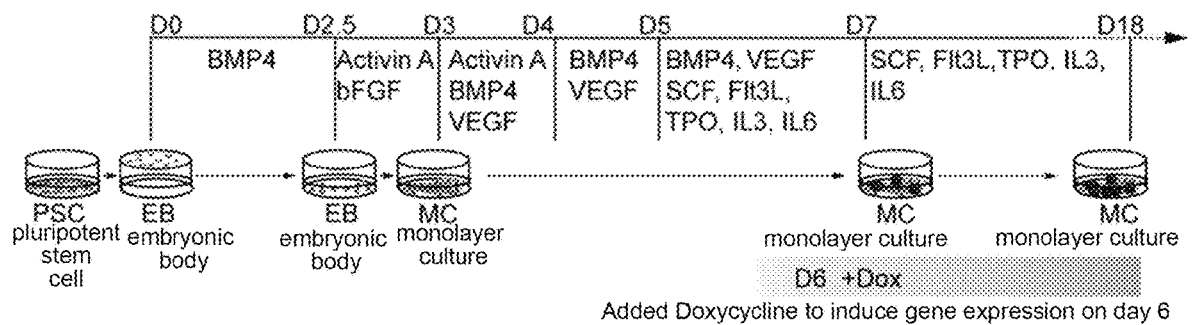
FIG. 2 (A) is a schematic diagram showing the embryoid body-monolayer culture system for inducing iRunx1-p2a-Hoxa9 pluripotent stem cells to directionally differentiate into hematopoietic precursors, hematopoietic stem cell precursors and blood cells.
Figure 2B:
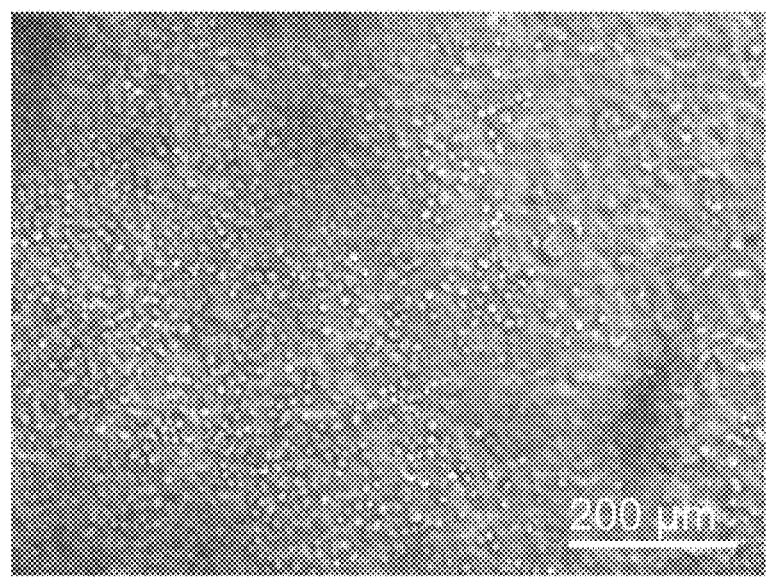
Figure 2C:
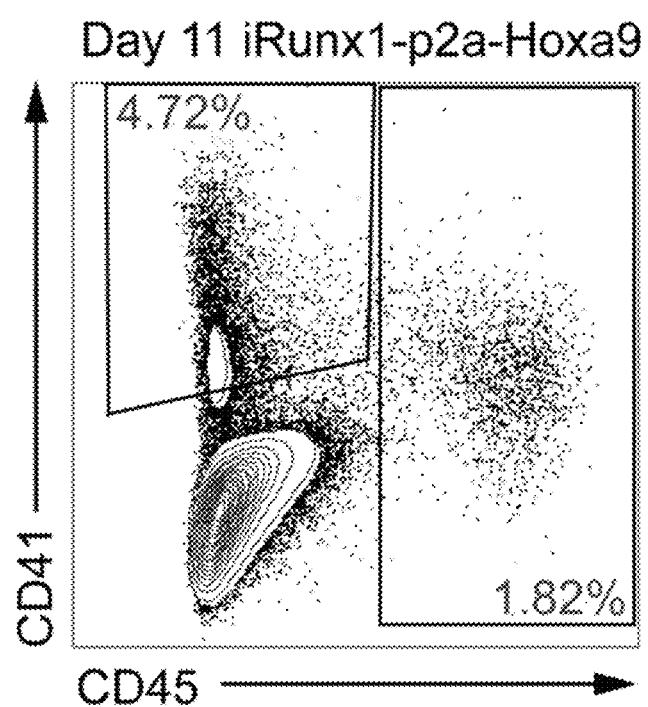
Figure 3A:
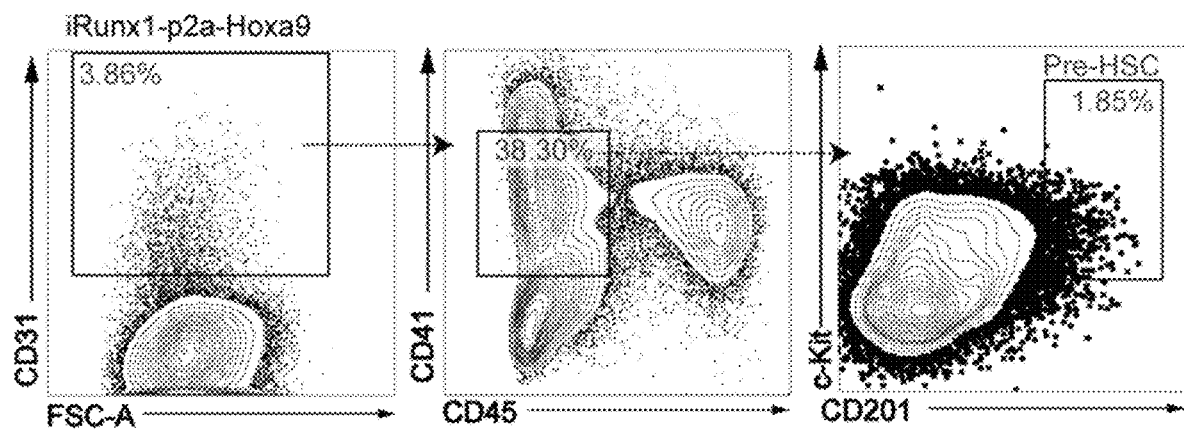
FIG. 3 (A) shows the flow cytometry sorting strategy for hematopoietic stem cell precursors.
Figure 3B:
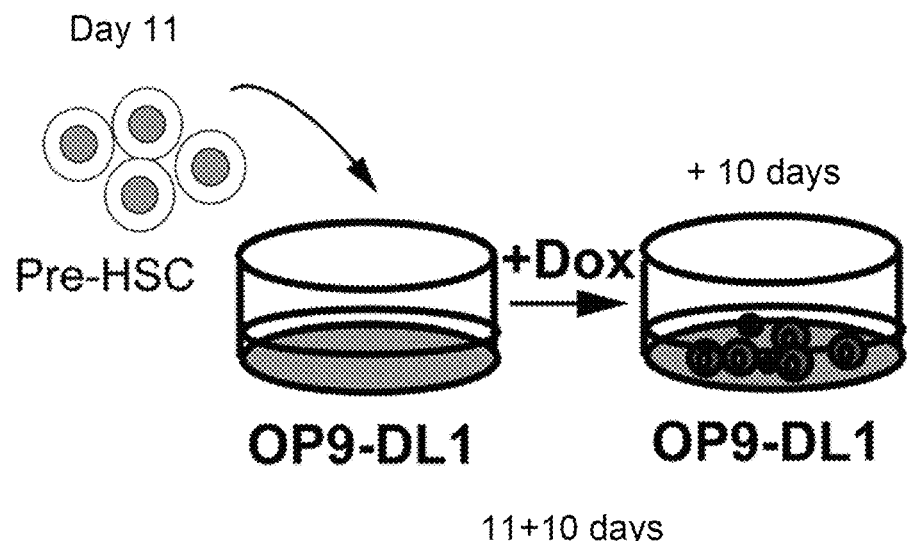
Figure 3C:
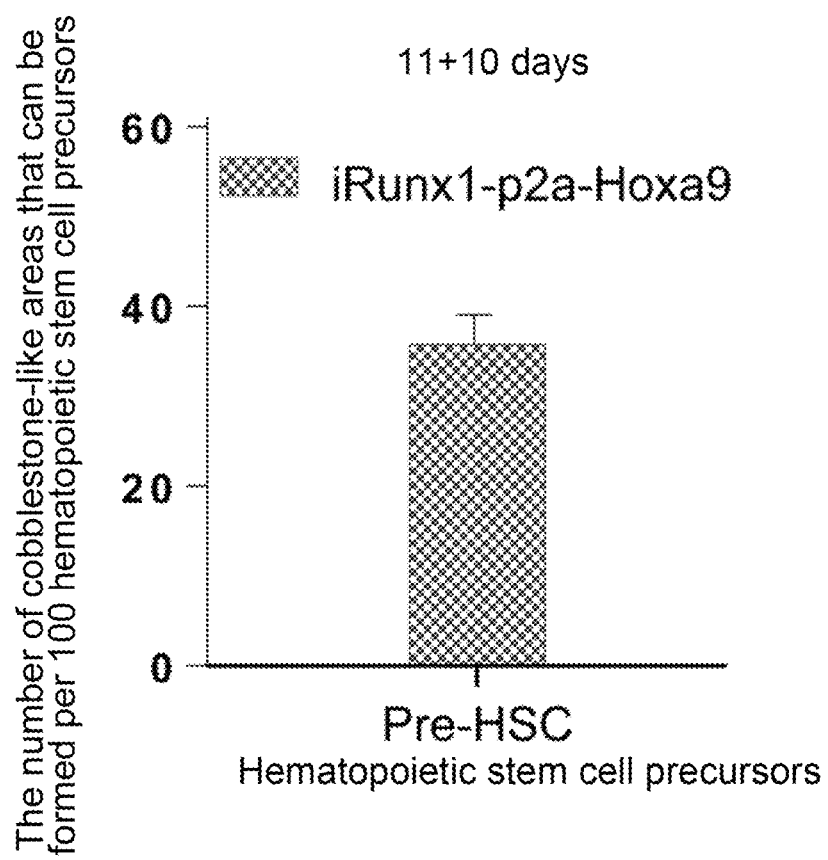
Figure 3D:
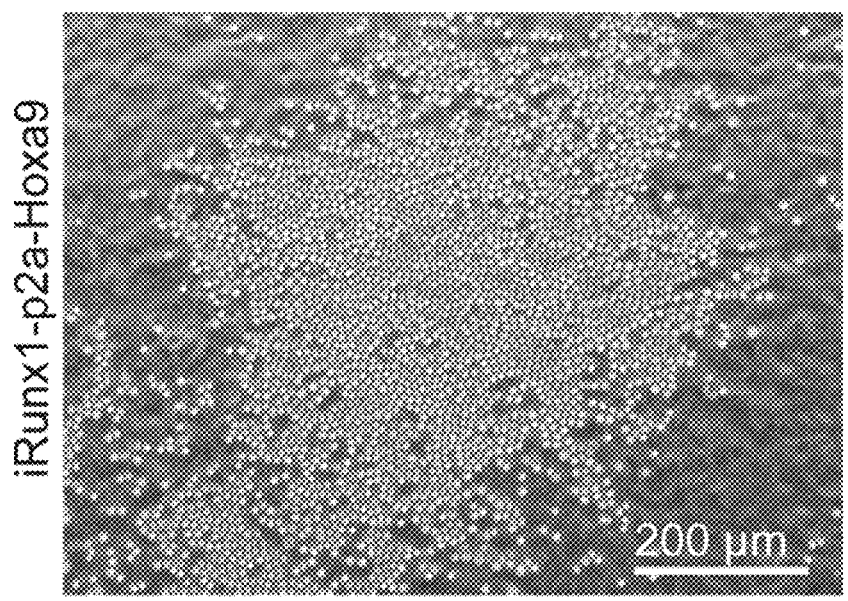
Figure 4A:
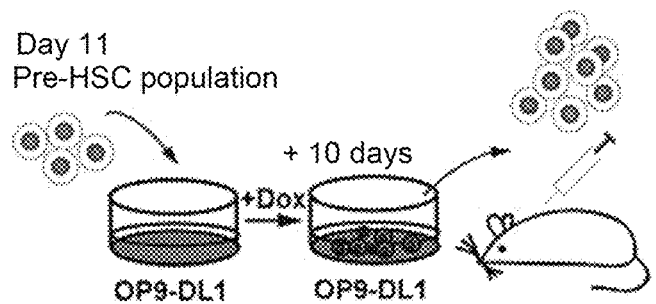
FIG. 4 (A) shows the transplantation of T-lineage progenitor cells which were harvested after the co-culture of hematopoietic stem cell precursors with OP9-DL1 cell line into a $CD45.1^+$ NOD/SCID immunodeficient mouse.
Figure 4B:
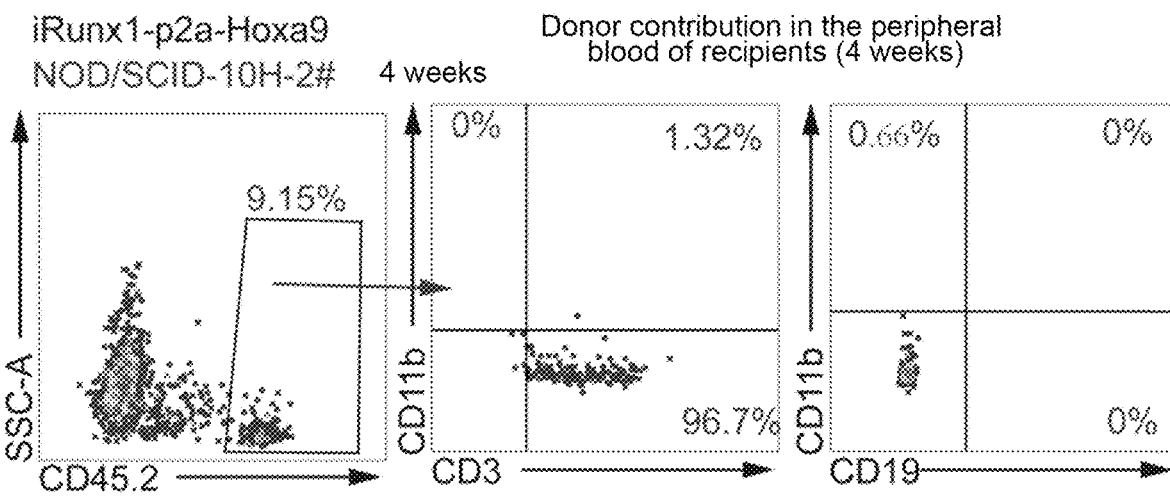
Figure 4C:
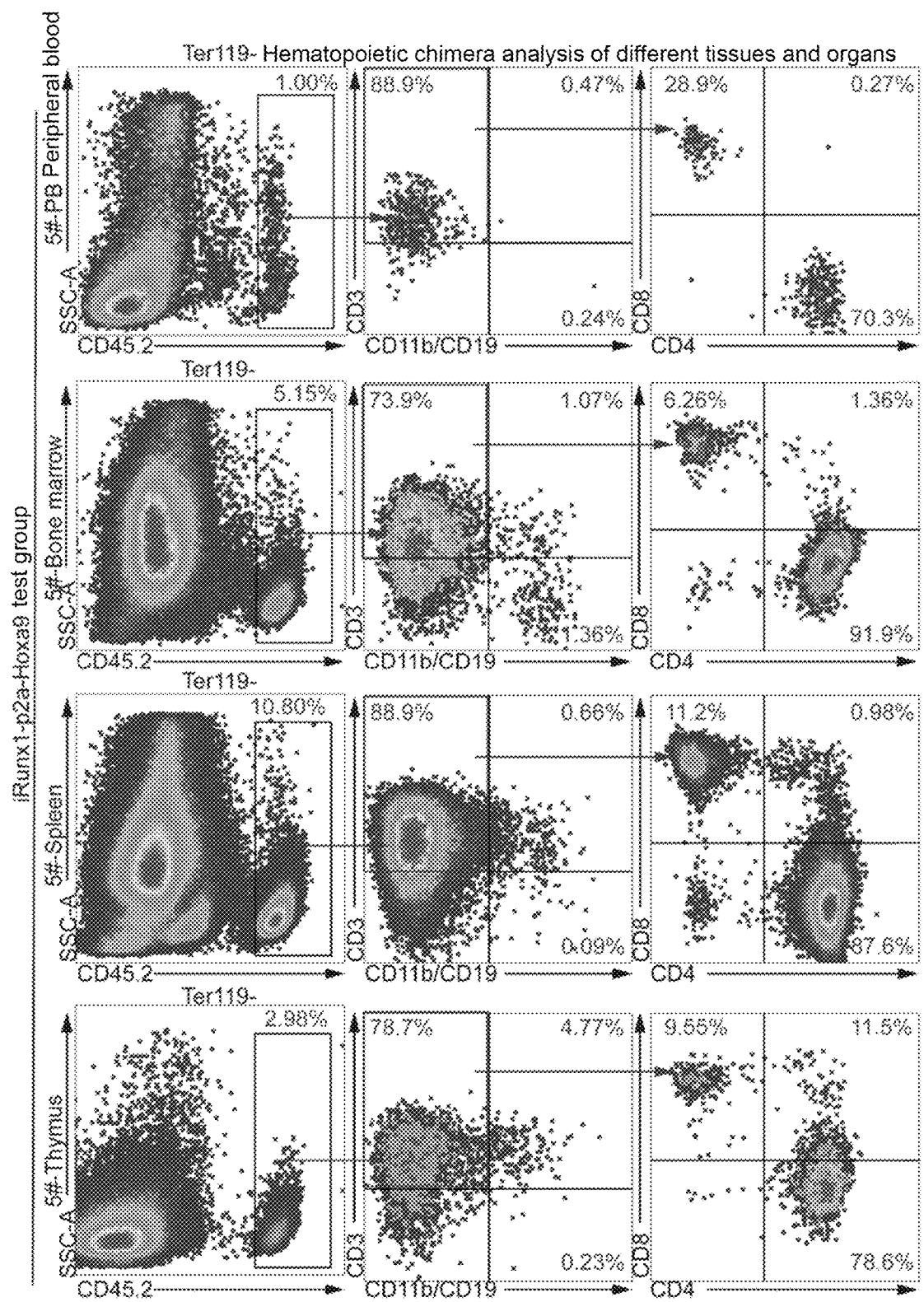
Figure 4D:
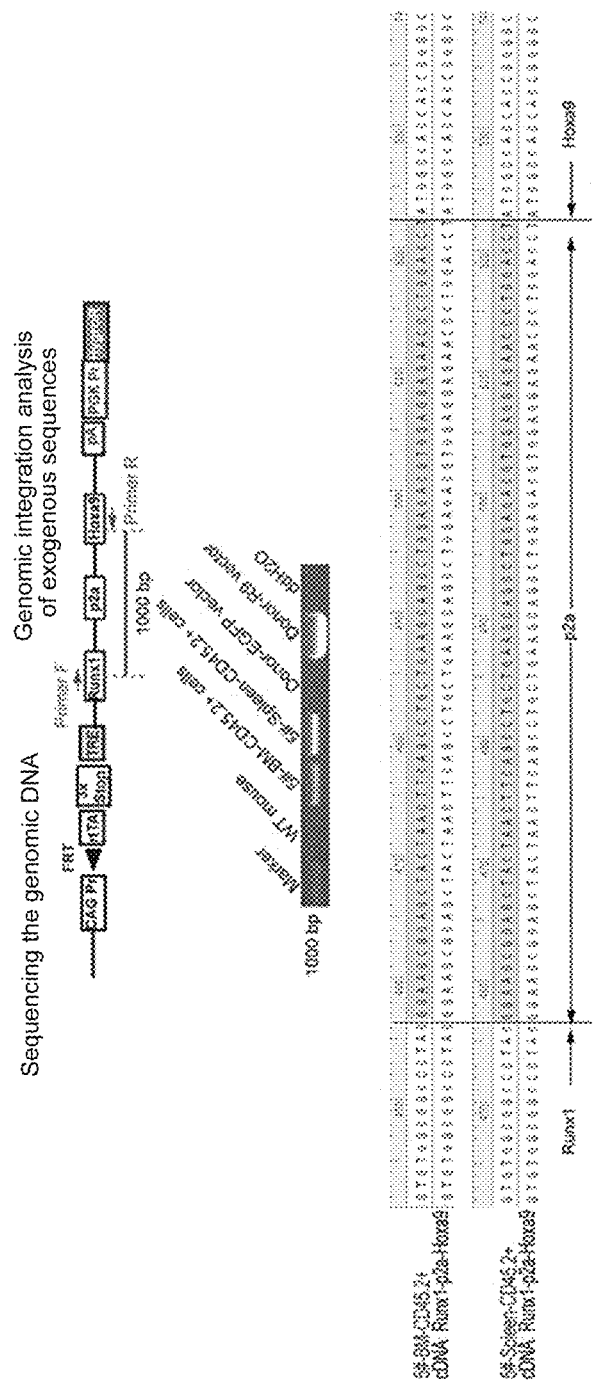

The directed hematopoietic differentiation system as shown in FIG. 2 (A) was used to induce the hematopoietic differentiation of pluripotent stem cells. The formulation of each medium in the directional hematopoietic differentiation system was:

Basic differentiation medium BDM: IMDM medium containing 15% fetal bovine serum, 200 µg/mL iron-saturated transferrin, $4.5 \times 10^{-4}$ M thioglycerol, 2 mM GlutaMAX™-I additive and 0.5 mM ascorbic acid;

D0 medium: a basal differentiation medium containing 5 ng/mL bone morphogenetic protein 4;

D2.5 medium: a basic differentiation medium containing 5 ng/mL activin A and 5 ng/mL basic fibroblast growth factor;

D3 medium: a basal differentiation medium containing 5 ng/mL activin A, 5 ng/mL bone morphogenetic protein 4 and 5 ng/mL vascular endothelial growth factor;

D4 medium: a basal differentiation medium containing 5 ng/mL bone morphogenetic protein 4 and 5 ng/mL vascular endothelial growth factor;

D5 medium: a basal differentiation medium containing 5 ng/mL bone morphogenetic protein 4 and 5 ng/mL vascular endothelium growth factor, 20 ng/mL recombinant mouse interleukin 3, 20 ng/mL recombinant mouse interleukin 6, 20 ng/mL recombinant mouse stem cell factor, 20 ng/mL recombinant human thrombopoietin and 20 ng/mL hFlt3L;

D6 medium: a basal differentiation medium containing 5 ng/mL bone morphogenetic protein 4, 5 ng/mL intravascular growth factor, 20 ng/mL recombinant mouse interleukin 3, 20 ng/mL recombinant mouse interleukin 6, 20 ng/mL recombinant mouse stem cell factor, 20 ng/mL recombinant human thrombopoietin, 20 ng/mL hFlt3L and 1 µg/mL Doxycycline;

D7 medium: a basal differentiation medium containing 20 ng/mL recombinant mouse interleukin 3, 20 ng/mL recombinant mouse interleukin 6, 20 ng/mL recombinant mouse stem cell factor, 20 ng/mL recombinant human thrombopoietin, 20 ng/mL hFlt3L and 1 µg/mL Doxycycline.

The specific steps were as follows:

1 mL of 0.1% gelatin was placed in a 6-well plate 40 min before use. The pluripotent stem cells were digested into single cells with 0.05% trypsin, centrifuged and resuspended. The 0.1% gelatin was aspirated, and the pluripotent stem cell suspension was transferred into a gelatin-coated well and placed in an incubator for 40 min to remove MEF cells.

The suspended cells were collected, centrifuged at 250 g for 5 min, and washed once with DPBS. The cells were resuspended with D0 medium and counted, and the cell concentration was adjusted to $1 \times 10^5$/mL. Added 5-10 mL of cell suspension into a tilted 10 cm dish, pipetted 20 µL of cell suspension and added the same into a 15 cm culture dish to suspend the embryoid body (EB) with 20 µL (about 2000 cells) per single EB. The culture dish was then inverted and a 10 cm culture dish lid was placed at the bottom of the culture dish and 5-6 mL of cell culture water was added into the lid. Incubated in an incubator at 37° C. for 2.5 days.

The EB was collected into a centrifuge tube with a Pasteur pipette, and the bottom of the dish was washed with DPBS. The supernatant was carefully aspirated when the EB has settled naturally. Alternatively, the supernatant was removed by centrifugation at a low speed of 90 g for 5 min. DPBS was added to rinse once. The supernatant was removed again by sediment or centrifugation. The EB was resuspended with D2.5 medium, transferred into a low-adherence 24-well plate and cultured for 12 hours to observe whether the EB was contaminated.

The EB was collected into a 15 mL centrifuge tube, and the supernatant was carefully aspirated when the EB has settled naturally. DPBS was added to rinse once. 400 µL of 0.05% trypsin was added, transferred into a 24-well low-adhesive culture dish and digested at 37° C. for 3 min, followed by repeated gentle blistering of the EB, and D3 medium was added to terminate the digestion when the EB exhibited a single cell state, centrifuged at 350 g for 5 min. The viable cells were resuspended with D3 medium and counted, and inoculated into a 12-well plate which was pre-coated with 0.1% gelatin at a density of $2 \times 10^5$ cells/well.

Rinsed with DPBS once, replaced with D4 medium and cultured for one day.

Rinsed with DPBS once, replaced with D5 medium and cultured for one day.

Rinsed with DPBS once, replaced with D6 medium and cultured for one day.

Rinsed with DPBS once, replaced with D7 medium and cultured for one day.

The medium was then replaced every other day with D7 medium. As shown in FIG. 2 (B), obvious hematopoietic clusters were observed in the iRunx1-p2a-Hoxa9 differentiation group on day 11; the flow cytometry analysis as shown in FIG. 2 (C) showed that the hematopoiesis-related cell populations were $CD41^+$ hematopoietic precursor cells and $CD45^+$ blood cells on day 11 of the directed differentiation.

Example 3

The inventors co-cultured hematopoietic stem cell precursors with mouse bone marrow stromal cells to verify that the hematopoietic precursor cells which were differentiated from pluripotent stem cells have the proliferative ability as an embryonic hematopoietic stem cell precursor population, that is, the ability to form cobblestone-like areas with high expansion potential on stromal cells. The co-culture medium was alpha-MEM medium containing 15% DFBS, 200 μg/mL iron-saturated transferrin, $4.5 \times 10^{-4}$ M thioglycerol, 2 mM GlutaMAX™-I additive, 0.5 mM ascorbic acid, 2% AFT024-mSCF conditioned medium, 2% AFT024-mIL3 conditioned medium, 2% AFT024-hFlt3L conditioned medium and 1 μg/mL Dox.

On day 11 of the embryoid body-monolayer culture, hematopoietic stem cell precursors ($CD31^+CD41^{low}/CD45^-$c-$Kit^+CD201^{high}$) were sorted by flow cytometry by using the sorting strategy as shown in FIG. 3 (A). Subsequently, a cobblestone-like area forming experiment (CAFC) was used to examine whether the hematopoietic stem cell precursors which were differentiated from pluripotent stem cells have the same proliferative ability as the embryonic-derived hematopoietic stem cell precursors. As shown in FIG. 3 (B), the sorted hematopoietic stem cell precursor population was re-plated onto OP9-DL1 stromal cells, and the number of the cobblestone-like areas formed per 100 hematopoietic stem cell precursors was counted 10 days later. The results in FIG. 3 (C) and FIG. 3 (D) indicated that the iRunx1-p2a-Hoxa9 pluripotent stem cell-derived hematopoietic stem cell precursors had a strong ability to form cobblestone-like areas, and the pluripotent stem cell-derived hematopoietic stem cell precursors formed highly uniform small, round and bright blood cells on stromal cells OP9-DL1.

Example 4

The inventors further designed a post-co-culture transplantation strategy to obtain T cells by utilizing the in vivo microenvironment. As shown in FIG. 4 (A), the hematopoietic stem cell precursors were placed onto the OP9-DL1 stromal cells and Dox was added for inducing for 10 days to obtain T-lineage progenitor cells. The OP9-DL1 cell line was resuscitated 4 days in advance, and the cells were passaged in time according to their growth state to prevent the cells from aging due to excessive growth. A passage was carried out one day before use by re-plating 50,000 cells per well (a 12-well plate) for use the next day. The T-lineage progenitor cells obtained by co-culture of the pluripotent stem cell-derived hematopoietic stem cell precursors were transplanted into a 6-8 weeks old CD45.1 NOD/SCID mouse via ocular vein, and the hematopoietic chimera of peripheral blood were detected by flow cytometry 4 weeks after the transplantation.

It was shown in FIG. 4 (B) that the T-lineage progenitor cells obtained by co-culturing the iRunx1-p2a-Hoxa9 pluripotent stem cell-derived hematopoietic stem cell precursor population formed hematopoietic chimera in the peripheral blood of the recipient NOD/SCID mouse, which were mainly CD3+ T cells (97.7%), achieving effective reconstruction of the T lymphatic system.

After 5 weeks, the mouse was sacrificed and the blood cell lineages in its peripheral blood, bone marrow, spleen and thymus were analyzed by flow cytometry to further clarify the distribution of iRunx1-p2a-Hoxa9 pluripotent stem cell-derived blood cells in other hematopoietic and lymphoid tissues. It was found in the flow cytometry analysis that, as shown in FIG. 4 (C), in the bone marrow, thymus and spleen, the pluripotent stem cell-derived blood cells were also mainly T-lineage hematopoiesis. This group of $CD3^+$ T cells, including both $CD4^+$ single positive cells and $CD8^+$ single positive cells, contained a small amount of both $CD4^+CD8^+$ double positive cells and $CD4^-CD8^-$ double negative cells in the spleen, bone marrow and thymus.

Primers were designed for PCR amplification and sequencing identification to confirm, from the genome level, that $CD45.2^+$ hematopoietic cells (mainly T cells) in the recipient mouse were derived from iRunx1-p2a-Hoxa9 pluripotent stem cells. First, bone marrow- and spleen-derived $CD45.2^+$ cells were sorted by flow cytometry, the genome thereof was extracted, and the specific primers of the knocked-in gene sequence were used for PCR identification. FIG. 4 (D) showed that iRunx1-p2a-Hoxa9 plasmid-derived sequences were found in the genome of these cells, confirming that the $CD45.2^+$ blood cells (primarily T cells) were derived from the iRunx1-p2a-Hoxa9 pluripotent stem cells.

Example 5

Figure 5A:
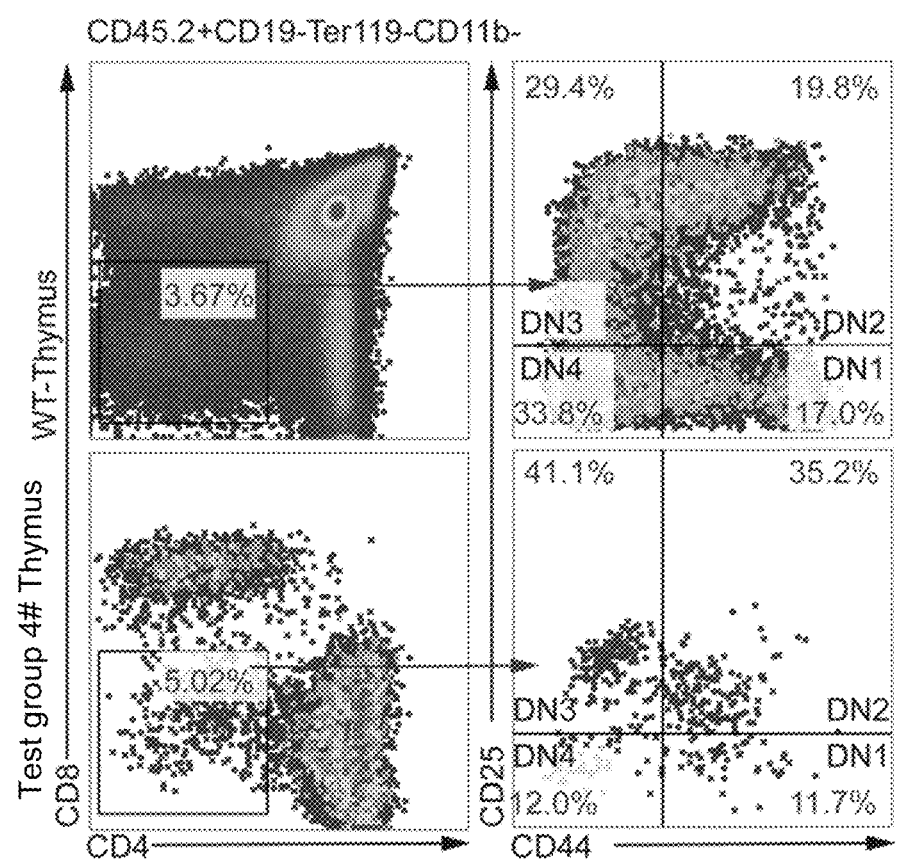
FIG. 5 (A) shows the analysis for the pluripotent stem cell-derived DN cell population (DN1/DN2/DN3/DN4) in the thymus of the recipient mouse which was sacrificed 4 weeks after the transplantation.
Figure 5B:
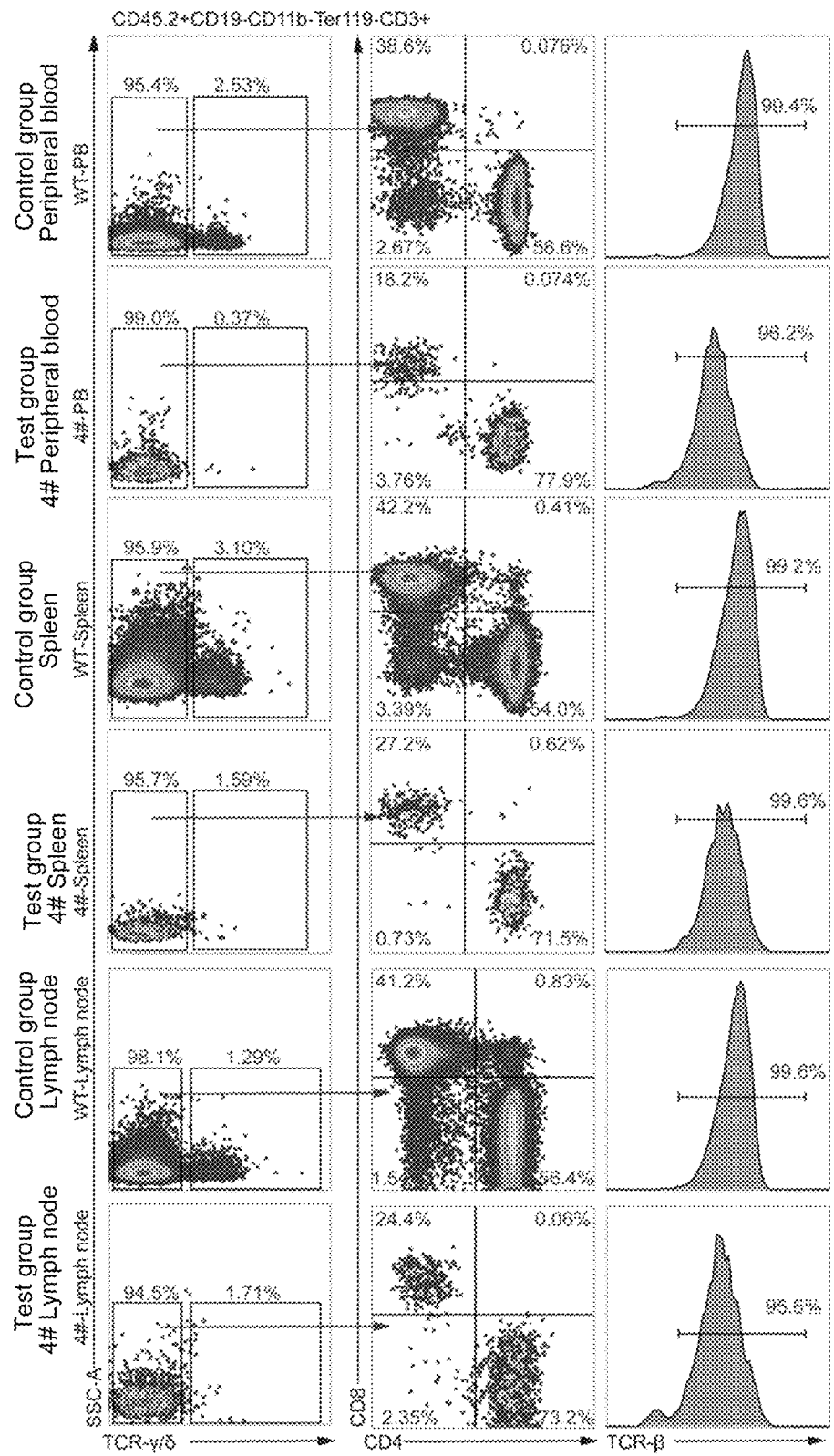
Figure 5C:
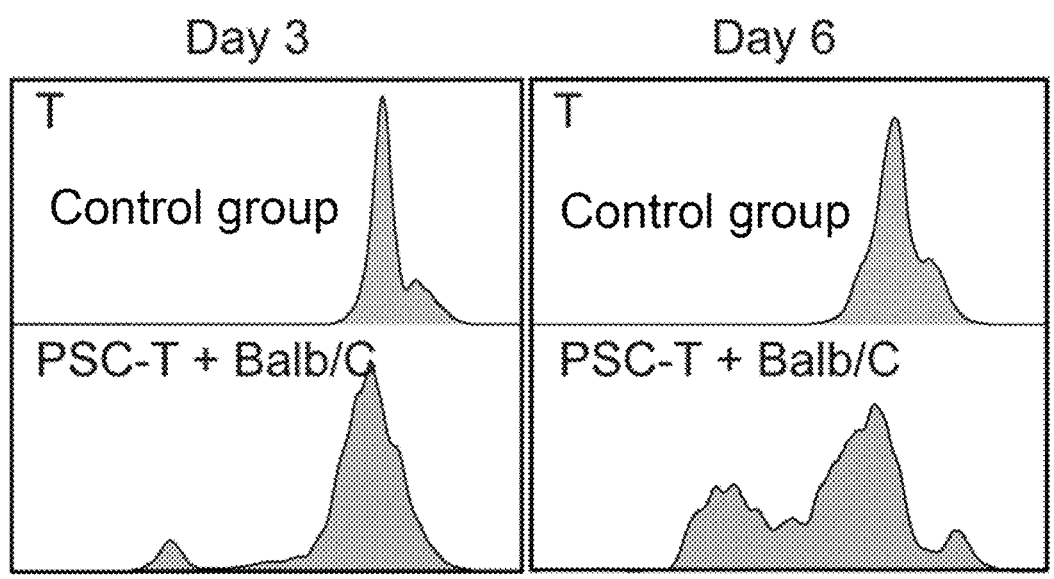

The thymus DN cell population was analyzed to further identify the type of the pluripotent stem cell-derived immune cells in the mouse. It was shown in FIG. 5 (A) that the T cells in the recipient mouse were normally developed and DN1, DN2, DN3 and DN4 cell populations were detectable. The TCR receptors of pluripotent stem cell-derived T cells in the peripheral blood, spleen and lymphatic vessels were subjected to a detection. As shown in FIG. 5 (B), a certain proportion of TCR γ/δ cells (0.37-1.71%) were found in the T cells, while most of them were TCR β cells. A mixed lymphocyte reaction was carried out with spleen cells of a Balb/C mouse and T cells obtained from the spleen of the recipient mouse by CD3 magnetic bead enrichment, and a detection was performed on days 3 and 6, respectively. As shown in FIG. 5 (C), the pluripotent stem cell-derived T cells were able to proliferate after activation, confirming that these T cells have proliferative ability after stimulation.

Figure 6:
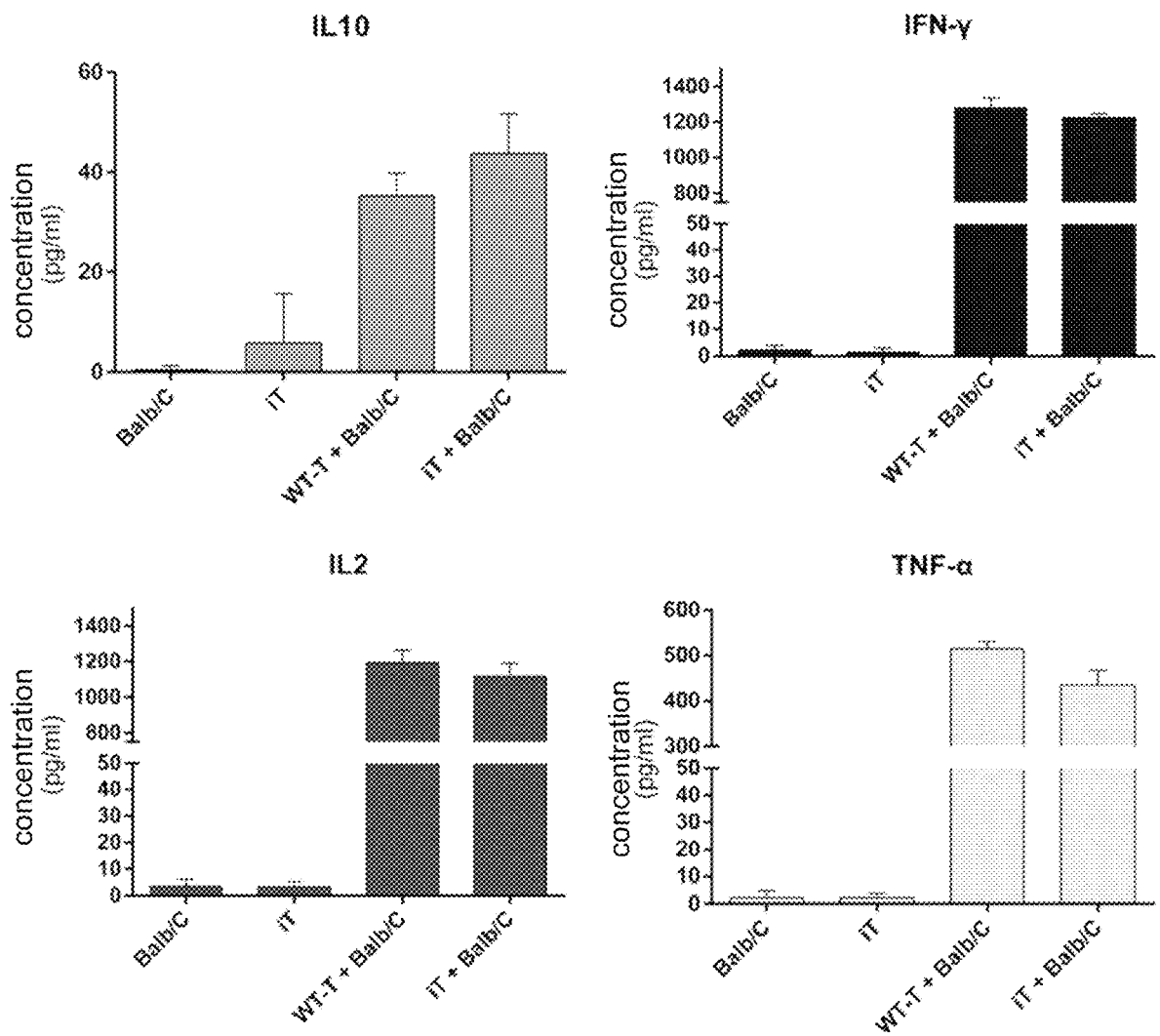
FIG. 6 shows the representative cytokines secreted by T cells after in vitro stimulation which are detected by ELISA, wherein IL10—interleukin 10, IFN-γ—γ interferon, IL-2—interleukin 2, TNF-α—tumor necrosis factor α.

The culture supernatant was analyzed by ELISA. As shown in FIG. 6, the regenerated T cells after stimulation and proliferation were able to secrete a large amount of interleukin 10 (IL10), interferon gamma (IFN-γ), interleukin 2 (IL-2) and tumor necrosis factor α (TNF-α).

In summary, pluripotent stem cells which inducibly co-express exogenous Runx1 and Hoxa9 are successfully constructed in the present invention by introducing an exogenous vector co-expressing Runx1 and Hoxa9 into pluripotent stem cells. The pluripotent stem cells were directionally differentiated into T-lineage progenitor cells which will be developed into T cells. The pluripotent stem cell-derived T cells obtained by the method of the present invention are not only functionally normal but also have no tumorigenic risk, and can be used for preparing a medicine for enhancing an immune effect, preventing and/or treating immunodeficiency and treating a tumor.

The applicant states that detailed methods of the present invention are demonstrate in the present invention through the above embodiments, however, the present invention is not limited to the above detailed methods, and does not mean that the present invention must rely on the above detailed methods to implement. It should be apparent to those skilled in the art that, for any improvement of the present invention, the equivalent replacement of the raw materials of the present invention, the addition of auxiliary components, and the selection of specific modes, etc., will all fall within the protection scope and the disclosure scope of the present invention.

The invention claimed is:

1. A method for directed differentiation of T cells using pluripotent stem cell, comprising the steps of:
   (1) integrating an expression vector wherein a nucleic acid sequence encoding Runx1 and a nucleic acid sequence encoding Hoxa9 are linked in tandem into pluripotent stem cells at a Rosa26 site by gene recombination and performing resistance screening with Hygromycin B;
   (2) culturing the pluripotent stem cells of step (1) with D0 medium, D2.5 medium, D3 medium, D4 medium, D5 medium, D6 medium and D7 medium sequentially, and directionally differentiating the same into hematopoietic stem cell precursors on day 11;
   (3) co-culturing the hematopoietic stem cell precursors of step (2) with OP9-DL1 cells and inducing with Doxycycline for at least 10 days to induce expression of Runx1 and Hoxa9 to obtain T-lineage progenitor cells; and
   (4) inducing the T-lineage progenitor cells of step (3) to differentiate into T cells, which are TCR β cells and/or TCR γ/δ cells,
   wherein:
   the D0 medium is a basic differentiation medium containing 3-8 ng/mL bone morphogenetic protein 4;
   the D2.5 medium is a basic differentiation medium containing 3-8 ng/mL activin A and 3-8 ng/mL basic fibroblast growth factor;
   the D3 medium is a basic differentiation medium containing 3-8 ng/mL Activin A, 3-8 ng/mL bone morphogenetic protein 4 and 3-8 ng/mL vascular endothelial growth factor;
   the D4 medium is a basic differentiation medium containing 3-8 ng/mL bone morphogenetic protein 4 and 3-8 ng/mL vascular endothelial growth factor;
   the D5 medium is a basic differentiation medium containing 3-8 ng/mL bone morphogenetic protein 4, 3-8 ng/mL vascular endothelial growth factor, 10-30 ng/mL recombinant mouse interleukin 3, 10-30 ng/mL recombinant mouse interleukin 6, 10-30 ng/mL recombinant mouse stem cell factor, 10-30 ng/mL recombinant human thrombopoietin and 10-30 ng/mL human Fms-associated tyrosine kinase 3 ligand;
   the D6 medium is a basic differentiation medium containing 3-8 ng/mL bone morphogenetic protein 4, 3-8 ng/mL vascular endothelial growth factor, 10-30 ng/mL recombinant mouse interleukin 3, 10-30 ng/mL recombinant mouse interleukin 6, 10-30 ng/mL recombinant mouse stem cell factor, 10-30 ng/mL recombinant human thrombopoietin, and 10-30 ng/mL human Fms-associated tyrosine kinase 3 ligand and 1-2 µg/mL Doxycycline;
   the D7 medium is a basic differentiation medium containing 10-30 ng/mL recombinant mouse interleukin 3, 10-30 ng/mL recombinant mouse interleukin 6, 10-30 ng/mL recombinant mouse stem cell factor, 10-30 ng/mL recombinant human thrombopoietin, and 10-30 ng/mL human Fms-associated tyrosine kinase 3 ligand and 1-2 µg/mL Doxycycline; and
   the basic differentiation medium is IMDM medium comprising 10-20% fetal calf serum, 180-220 µg/mL iron-saturated transferrin, $4.5\times10^{-4}$ M thioglycerol, 2 mM L-alanyl-L-glutamine dipeptide, and 0.5 mM ascorbic acid.

2. The method of claim 1, wherein the D0 medium is a basic differentiation medium containing 5 ng/mL bone morphogenetic protein 4.

3. The method of claim 1, wherein the D2.5 medium is a basic differentiation medium containing 5 ng/mL activin A and 5 ng/mL basic fibroblast growth factor.

4. The method of claim 1, wherein the D3 medium is a basic differentiation medium containing 5 ng/mL Activin A, 5 ng/mL bone morphogenetic protein 4 and 5 ng/mL vascular endothelial growth factor.

5. The method of claim 1, wherein the D4 medium is a basic differentiation medium containing 5 ng/mL bone morphogenetic protein 4 and 5 ng/mL vascular endothelial growth factor.

6. The method of claim 1, wherein the D5 medium is a basic differentiation medium containing 5 ng/mL bone morphogenetic protein 4, 5 ng/mL vascular endothelial growth factor, 20 ng/mL recombinant mouse interleukin 3, 20 ng/mL recombinant mouse interleukin 6, 20 ng/mL recombinant mouse stem cell factor, 20 ng/mL recombinant human thrombopoietin and 20 ng/mL human Fms-associated tyrosine kinase 3 ligand.

7. The method of claim 1, wherein the D6 medium is a basic differentiation medium containing 5 ng/mL bone morphogenetic protein 4, 5 ng/mL vascular endothelial growth factor, 20 ng/mL recombinant mouse interleukin 3, 20 ng/mL recombinant mouse interleukin 6, 20 ng/mL recombinant mouse stem cell factor, 20 ng/mL recombinant human thrombopoietin, and 20 ng/mL human Fms-associated tyrosine kinase 3 ligand and 1 µg/mL Doxycycline.

8. The method of claim 1, wherein the D7 medium is a basic differentiation medium containing 20 ng/mL recombinant mouse interleukin 3, 20 ng/mL recombinant mouse interleukin 6, 20 ng/mL recombinant mouse stem cell factor, 20 ng/mL recombinant human thrombopoietin, 20 ng/mL human Fms-associated tyrosine kinase 3 ligand and 1 µg/mL Doxycycline.

9. The method of claim 1, wherein the basic differentiation medium is IMDM medium comprising 15% fetal calf serum, 200 µg/mL iron-saturated transferrin, $4.5\times10^{-4}$ M thioglycerol, 2 mM L-alanyl-L-glutamine dipeptide, and 0.5 mM ascorbic acid.

10. The method of claim 1, wherein the pluripotent stem cells in step (1) are genetically-edited inducible pluripotent stem cells or embryonic pluripotent stem cell lines.

* * * * *